United States Patent
Martinez Arenas

(10) Patent No.: US 11,412,741 B2
(45) Date of Patent: Aug. 16, 2022

(54) **BIOCIDE COMPOSITION FOR CONTROLLING PESTS AFFECTING EUROPEAN HONEY BEES, CONSISTING OF A WATER-SOLUBLE *OLEA EUROPAEA* EXTRACT**

(71) Applicant: UNIVERSIDAD DEL DESARROLLO, Santiago (CL)

(72) Inventor: Jessica Isabel Martinez Arenas, Santiago (CL)

(73) Assignee: UNIVERSIDAD DEL DESARROLLO, Santiago (CL)

( * ) Notice: Subject to any disclaimer, the term of this patent is extended or adjusted under 35 U.S.C. 154(b) by 795 days.

(21) Appl. No.: 15/115,485

(22) PCT Filed: Jan. 19, 2015

(86) PCT No.: PCT/CL2015/050003
§ 371 (c)(1),
(2) Date: Feb. 1, 2017

(87) PCT Pub. No.: WO2015/113175
PCT Pub. Date: Aug. 6, 2015

(65) Prior Publication Data
US 2017/0164622 A1 Jun. 15, 2017
US 2022/0087270 A9 Mar. 24, 2022

(30) Foreign Application Priority Data

Jan. 30, 2014 (CL) .................................... 243-2014

(51) Int. Cl.
*A01N 65/08* (2009.01)
*A01N 25/08* (2006.01)
*A01N 43/16* (2006.01)
*A61K 36/63* (2006.01)

(52) U.S. Cl.
CPC ............ *A01N 65/08* (2013.01); *A01N 25/08* (2013.01); *A01N 43/16* (2013.01); *A61K 36/63* (2013.01); *Y02A 50/30* (2018.01)

(58) Field of Classification Search
USPC ........................................................ 424/411
See application file for complete search history.

(56) References Cited

U.S. PATENT DOCUMENTS

| 5,188,832 A | * | 2/1993 | Mehlhorn | ............ | A61K 31/535 |
| | | | | | 424/405 |
| 2007/0232188 A1 | | 10/2007 | Probasco | | |
| 2008/0026673 A1 | * | 1/2008 | Probasco | ............... | A01K 51/00 |
| | | | | | 449/2 |
| 2009/0104288 A1 | * | 4/2009 | Probasco | ............... | A01N 65/08 |
| | | | | | 424/725 |
| 2009/0131539 A1 | * | 5/2009 | Schutz | ................... | A01N 31/02 |
| | | | | | 514/731 |
| 2012/0183627 A1 | * | 7/2012 | Rizza | .................... | A61K 9/0031 |
| | | | | | 424/641 |

FOREIGN PATENT DOCUMENTS

| EP | 2735229 A1 | 5/2014 | |
| WO | 99/38383 | 8/1999 | |
| WO | WO-2013030854 A1 | * 3/2013 | ............. A01K 53/00 |

OTHER PUBLICATIONS

Flesar et al..Veterinary Microbiology, vol. 145, Issues1-2, Sep. 28, 2010, pp. 129-133.*
Markin et al. ,Mycoses, 46, pp. 132-136, 2003.*
John Misachi, The Important Features Of The Mediterranean Climate. [online], Aug. 1, 2017 [retrieved on Jan. 2, 2019], Retrieved from the Internets URL:https://www.worldatlas.com/articles/the-important-features-of-the-mediterranean-climate.html>.*
Ptimum Climate and Olive Varietiesclimatic Factors [online], [retrieved on Jan. 2, 2019], Retrieved from the Internet: <URLhttps://www.mcevoyranch.com/about/farming-practices/optimum-climate-and-olive-varieties>.*
Flesar et al. "In vitro growth-inhibitory effect of plant-derived extracts and compounds against Paenibacillus larvae and their acute oral toxicity to adult honey bees", Veterinary Microbiology 145, pp. 129-133, 2010.
Markin et al. In vitro antimicrobial activity of olive leaves, Mycoses, 46, pp. 132-136, 2003.
Aliabadi et al. "Antimicrobial activity of olive leaf aqueous extract", Annals of Biological Research, 2012, 3 (8), pp. 4189-4191, 2012.
Bisignano et al. "On the In-vitro Antimicrobial Activity of Oleuropein and Hydroxytyrosol", J. Pharm. Pharmacol. 51, pp. 971-974, 1999.
Sudjana et al. "Antimicrobial activity of commercial *Olea europaea* (olive) leaf extract", International Journal of Antimicrobial Agents 33 pp. 461-463, 2009.
Mourtzinos et al. "Encapsulation of Olive Leaf Extract in β-Cyclodextri", J. Agric. Food Chem. 55, pp. 8088-8094, 2007.
International Search Report, dated May 22, 2015, International Patent Application No. PCT/CL2015/050003 with English translation (7 pages).

(Continued)

*Primary Examiner* — Johann R Richter
*Assistant Examiner* — Courtney A Brown
(74) *Attorney, Agent, or Firm* — Procopio, Cory, Hargeaves & Savitch LLP

(57) ABSTRACT

The aim of the invention is to provide a biocide composition which consists of a commercial natural olive leaf extract (*olea europea*) and a carrier which allows administering the plant extract in the beehive, preferably syrup (50% w/v sucrose dissolution) to inhibit the growth of the *Paenibacillus larvae* bacteria in all the phases of its biological cycle, both in its vegetative state and as a spore, along with *Melissococcus plutomius* and/or *Nosema* spp. achieving a curative treatment or the prophylaxis of the disease in the *Apis mellifera larvae* and adult bees. The active substance is preferably oleuropein, a secoiridoid glucoside, naturally present in plants of the Oleaceae family, although in lower concentrations.

9 Claims, 6 Drawing Sheets

(56) References Cited

OTHER PUBLICATIONS

Figure 1:
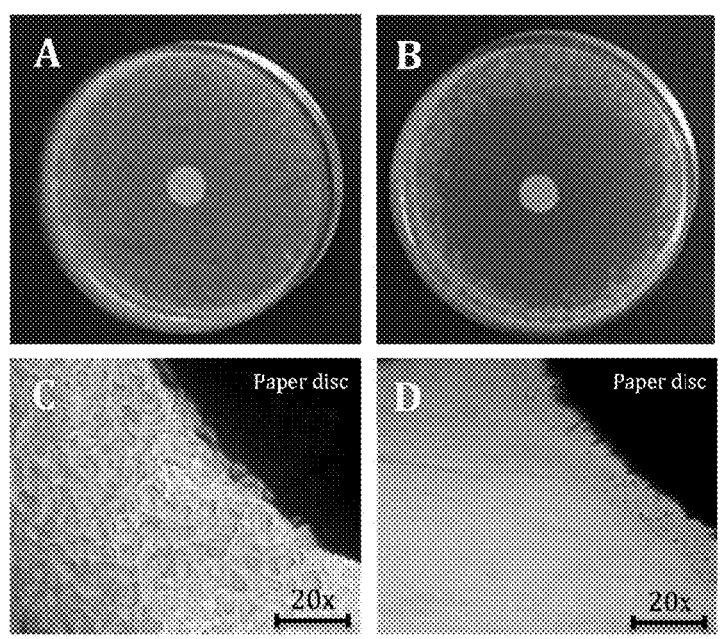

Written Opinion of the International Searching Authority, dated May 22, 2015, International Patent Application No. PCT/CL2015/050003 with English translation (14 pages).

Colmagro, S. et al., "Processing Technology of the Table Olive," Horticultural Reviews, vol. 25, 2001, ISBN 0-471-34933-X, pp. 235-242, 8 pages.

Ghomari, O. et al., "Phenolic profile (HPLC-UV) of olive leaves according to extraction procedure and assessment of antibacterial activity," Biotechnology Reports 23, 2019, e00347, https://doi.org/10.1016/j.btre.2019.e00347, 7 pages.

Supplementary European Search Report for related Application No. EP 15 74 3991, dated Aug. 2, 2017, in 2 pages.

European Search Opinion for related Application No. EP 15 74 3991, dated Sep. 12, 2018, in 3 pages.

\* cited by examiner spores

FIGURE 4

|  | Inhibitor concentrations | | | | | | | | | | | |
|---|---|---|---|---|---|---|---|---|---|---|---|---|
| Microorganisms | 1 | 2 | 3 | 4 | 5 | 6 | 7 | 8 | 9 | 10 | 11 | 12 |
| P. larvae (vegetative cells) | + | + | + | + | 0 | 0 | 0 | 0 | 0 | 0 | 0 | 0 |
| P. larvae (spores) | + | + | + | + | + | + | 0 | 0 | 0 | 0 | 0 | 0 |
| M. plutonius | + | + | + | + | + | + | + | + | + | + | 0 | 0 |
| P. alvei | + | + | + | + | + | + | 0 | 0 | 0 | 0 | 0 | 0 |

+. Growth is observed; 0. No growth is observed

FIGURE 5

|  | Inhibitor concentrations | | | | | | | |
|---|---|---|---|---|---|---|---|---|
| Microorganisms | 1 | 2 | 3 | 4 | 5 | 6 | 7 | 8 |
| B. megaterium | + | + | + | + | + | + | + | + |
| B. subtilis | + | + | + | + | + | + | + | + |
| B. pumilus | + | + | + | + | + | + | + | + |
| P. polymyxa | + | + | + | + | + | + | + | + |

+. Growth is observed; 0. No growth is observed

BIOCIDE COMPOSITION FOR CONTROLLING PESTS AFFECTING EUROPEAN HONEY BEES, CONSISTING OF A WATER-SOLUBLE *OLEA EUROPAEA* EXTRACT

CROSS-REFERENCE TO RELATED APPLICATIONS

This Application is a National Stage Entry of PCT Application PCT/CL2015/050003, filed Jan. 19, 2015, and which claims priority to Chile Application 2A3-2014, filed Jan. 30, 2014.

This invention refers to a biocide composition to inhibit the growth of the *P. larvae* bacteria, both vegetative cells and spores, *Nosema* sp and/or the bacteria of *Melisococcus plutonius*. This composition comprises the combination of a commercial olive leaf extract (*Olea europaea*), whose main component (40%) is a secoiridoid glucoside, oleuropein, in a biocompatible carrier, with the addition of other components not being necessary.

According to the merits of this invention, the composition can be produced industrially and marketed as a reagent to be used for the following purposes:

1. Food supplement of *larvae* and *A. mellifera* adult bees.
2. Preventative and curative control of the infection of *A. Mellifera larvae* by *P. larvae* and *M. plutonius*, as well as the preventative and curing control for the infection of *A. Mellifera* adult bees by *Nosema* spp.
3. Disinfection of beehive equipment.

STATE-OF-THE-ART

The European honeybee (*Apis mellifera*), together with the Asiatic honey bee (*Apis cerana*) are the basis of the honey-making industry (Ellis and Munn, 2005). The two main aspects of economic sustainability for breeding bees are pollination and honey production (Reynaldi et al, 2008). Increasingly, other products of the hives including pollen, propolis, Queen Bees are being sold (Genersh, 2010, Genersch et al, 2010).

One of the biggest challenges of the honey-making industry is that bees, in their different stages of development, are exposed to a wide range of pathogens (viruses, bacteria, fungi, microsporidia, arthropod parasites, etc.) which weaken the hives' populations (Gilliam et al, 1977). One of the bacterial diseases causing great concern for beekeepers and government agencies around the world is American Foulbrood (Lindstrom I, 2008). Its causal agent is the *Paenibacillus larvae*, a *larvae* sub species, gram positive spore forming bacteria, belonging to the *Bacillus* group (Genersch et al, 2006; Bailey, 1962). The spores (considered as the infective stage of *P. larvae*) are highly resistant to heat and dehydration, can lie dormant for decades (Haseman, 1961), both in beekeeping equipment and in the cells of the hive's frames. The disease attacks the bees' *larvae* which are infected by ingesting spores, causing their death.

Currently the procedures that are available to treat the disease range from the most drastic ones, removal of diseased hives and the equipment associated to their handling by incineration, the sterilization of the hives and their contents using chemical products (formaldehyde, chlorine, ethylene oxide), and the prophylactic and therapeutic use of antibiotics. All these treatments have limitations associated to their use, including: i) economic losses due to the destruction of the burnt colonies; ii) generation of resistant strains, antibiotics have shown limited effectiveness in the field (Hansen and Broadsgaard, 1999). In Argentina and the United States, the appearance of strains of *P. larvae* resistant to tetracycline, oxytetracycline and sulfathiazole (Alippi, 1996; Miyagi et al, 2000) has been reported. This is mainly because the *P. larvae* spores are resistant to these and can remain in the hive and the equipment spreading the infection; iii) adverse effects associated to the accumulation of toxic chemicals and of antibiotic waste in the hives (honey and pollen), which affect the quality of the honey produced (Jimenez et al, 2006) and that cause alterations in the bees' behavior, including the abandonment of hives and a reduction of the colony's total population (Bastos et al, 2008). The latter effect is explained by high mortality in offspring. In contrast, this invention, detailed below—i) inhibits the growth of the bacteria, *Paenibacillus larvae* and *Melissococcus plutonius* and the germination of *P. larvae* spores; ii) inhibits the growth and proliferation of the fungus, *Nosema ceranae*; iii) the composition is stable during the period that it must be used in; iv) the stock composition does not experience major changes through time; v) it is effective for the curative treatment or prophylaxis of the disease; vi) is selective; vii) is harmless for the *larvae* and adult bees; viii) its administration is consistent with the colony's foraging for food; ix) it can be administered to any component of the hive (for example occupied or unoccupied honeycombs) or to the group of bees itself. That is to say, the invention has clear advantages over treatments used currently, both in terms of its use and its effectiveness and harmlessness.

This invention is directed to a composition comprising a commercially available olive leaf extract (*Olea europaea*), which includes as its main active ingredient, Oleuropein, a naturally occurring secoiridoid glucoside component, to inhibit the growth of pathogens which affect both *larvae* and adult honeybees given that:

The olive leaf extract has been shown to have strong in vitro antimicrobial properties against viruses, gram negative and positive bacteria, yeast and parasites, both in animals and in humans. It has also been shown to alter bacterial spore germination delaying the organism's growth.

The olive leaf extract has phenolic components; the main active phenol component in the olive leaf is Oleuropein and its derivatives, such as hyroxytyrosol and tyrosol, which gives the extract its antimicrobial properties.

It has been shown to be non-toxic in animal experiments (in high doses (1 g/kg body weight) during a week's treatment), and in cultures of human cell lines (at 1 mg/ml of extract).

It is consumed as a dietary supplement in humans as has numerous cardiovascular benefits, hypoglycemic and antioxidant activity.

Oleuropein is found in high quantities in all the parts of the olive tree, especially in the leaves (6-9% p/p dry leaf).

A Hydroxytyrosol metabolite of Oleuropein has recently been proven to be effective against human pathogens, *Haemophilus influenzae, Salmonella typhi, Vibrio parahaemolyticus* and *Staphylococcus aureus* ( ).

Oleuropein and its derivatives have demonstrated in vitro antimicrobial effectiveness and, therefore, may have application in the treatment of infections of *Apis mellifera larvae*.

The only two documents currently available relating to a) antimicrobial activity of commercial olive leaf extract and b) antimicrobial activity of olive leaf extract (obtained with organic solvents) against *P. larvae* are presented and discussed below:

"Antimicrobial activity of commercial *Olea europaea* (Olive) leaf extract". Aurelia N. Sudjana et al, 2009: the in vitro antimicrobial activity of a commercial liquid extract of olive leaves was investigated with a guaranteed minimum oleuropein content (4.4 mg/ml) against a wide range of microorganisms; *P. larvae* was not considered. It is shown that the extract does not have a broad spectrum of action, being shown to only be effective against *C. Jejuni, H. Pylori* and *Staphylococcus* spp. Furthermore, in this table, what is described in the aforementioned scientific article versus this invention is compared in detail.

|  | Sudjana et al, 2009 | This invention |
|---|---|---|
| Objective | Investigate the antimicrobial activity of a commercial extract derived from *Olea europaea* (olive) leaves, against a wide range of micro-organisms that does not include *P. larvae*. | Inhibit the growth of *P. larvae* and *M. plutonius* with a commercial extract of *Olea europaea* (olive) leaves, whose main active ingredient is Oleuropein |
| Type of organisms | Bacterial strains | Bacterial strains |
| Pathogen | *Campylobacter jejuni* *Helicobacter pylory* *Staphylococcus aureus* and another 30 organisms | *P. larvae* *M. plutonius* |
| Toxicity test | Was not done | Was done on larvae |
| Olive leaf extract | Liquid commercial contract (guaranteed minimum oleuropein content (4.4 mg/ml)) | Commercial powder extract. Oleuropein (400 mg/ml) |
| Exposure time | 3 days | 5 days |
| Outcomes | i) antimicrobial activity ii) minimum inhibitory concentration iii) selectivity | i) antimicrobial activity ii) minimum inhibitory concentration iii) selectivity |
| Results | The exposure to the extract results in: i) inhibition in the growth of, *C. Jejuni, H. Pylory* and *Stapylococcus* spp. ii) the minimum inhibitory concentration was ≥50 v/v in the less susceptible organisms and between 0.31 and 0.78 v/v in susceptible organisms. iii) A broad activity spectrum is not shown | The exposure to the extract results in: i) in regards to antimicrobial activity: Inhibition of the growth of *P. larvae* vegetative cells Inhibition of the growth of *P. larvae* spores Inhibition of the growth of *M. plutonius* The minimum inhibitory concentration was ≥2% w/v in the least susceptible organisms and ≤0.1% w/v in susceptible organisms iii) A broad activity spectrum is not shown |
| Conclusion | i) This is effective only for *C. Jejuni, H. Pylory* and *Staphylococcus* spp ii) the susceptibility data obtained does not allow stating that the extract is effective in therapies of a wide range of diseases | The extract inhibits the growth of *P. larvae* and *M. Plutonius*. The extract does not cause the death of the larvae even over the concentration that has antimicrobial activity facing the *P. larvae*. |

"In vitro growth-inhibitory effect of plant-derived extracts and compounds against *Paenibacillus larvae* and their acute oral toxicity to adult honey bees". Jaroslav Flesar et al, 2010: the antibacterial activity of the extract of raw *Olea europaea* leaves was assayed in vitro using the micro-dilution method, the extract was made using methanol:dichloromethane 1:1 and dissolved in DMSO at a concentration of 25.6 mg/ml. The MIC was defined as the lowest dilution which inhibits 80% of the growth compared to the control. The MIC of the olive leaf extract facing *P. larvae* was 256 µg/ml; one of the highest values when compared with another 16 assayed extracts. The olive leaf extract was not included in the toxicity tests for oral consumption in adult bees. This is where said work differs from the present invention in terms of how it is obtained and its composition, an aqueous extract is not used and nor is a commercial extract. Its toxicity is not tested either in *larvae* or adult *A. Mellifera* bees. Furthermore, in the following table, what is described in the aforementioned scientific article versus this invention is compared in more detail.

|  | Flesar et al, 2010 | This invention |
|---|---|---|
| Objective | In vitro assay, 26 natural components of several commercially available chemical classes (flavonoids, terpenoids, alkaloids) and 19 raw plant extracts (among these, the extract of *Olea europaea* (olive) leaves), due to their antimicrobial activity when facing *P. larvae*. | Inhibit the growth of *P. larvae* and *M. plutonius* with a commercial extract of *Olea europaea* (olive) leaves, whose main active ingredient is Oleuropein |
| Type of organisms | Bacterial strains | Bacterial strains |
| Pathogen | *P. larvae* | *P. larvae* *M. plutonius* |
| Toxicity test | In adult bees, only with two extracts. Not done with olive leaf extract | On larvae |
| Olive leaf extract | Collected and dried leaves, methanol-dichloromethane (1:1) extraction solvents, soluble in DMSO. concentration of active ingredient is unknown | Commercial powder extract. Ethanol and water extraction solvents water soluble Oleuropein (400 mg/ml) |
| Exposure time | 2 days | 5 days |
| Outcomes | i) antimicrobial activity ii) minimum inhibitory concentration | i) antimicrobial activity ii) minimum inhibitory concentration iii) selectivity |
| Results | The exposure to the extract results in: i) olive leaf extract was one of the least active facing the vegetative cells of *P. larvae* ii) the minimum inhibitory concentration was 256 µg/ml | The exposure to the extract results in: i) in regards to antimicrobial activity: Inhibition of the growth of *P. larvae* vegetative cells Inhibition of the growth of *P. larvae* spores Inhibition of the growth of *M. plutonius* ii) The minimum inhibitory concentration of the *P. larvae* vegetative cells was 80 µg/ml iii) A broad activity spectrum is not shown |
| Conclusion | i) In vitro effective natural products against *P. larvae* vegetative cells were identified. ii) the effective extracts were *Humulus lupulus L.* and *Myrtus communis L.* | i) The commercial olive leaf extract inhibits the growth of *P. larvae* (vegetative cells and spores) and *M. Plutonius* ii) the extract does not cause the death of the larvae at the same concentration which has antimicrobial activity |

"Compositions and methods for inhibiting a honey bee pathogen infection or controlling a hive infestation" patent WO2008060591: a composition is disclosed which prevents or treats pathogen infections or hive infestations using a derivative (an organic acid) of the hop plant (*Humulus lupulus*), an alpha acid, a beta acid or a combination thereof. The effective concentration of this derivative inhibits the growth, the proliferation of bacteria or fungi. In in vitro assays, the composition inhibited *Melissococcus plutonius, Paenibaccilus larvae*, or the fungus, *Ascosphaera apis*. In addition, it kills bacteria and fungi spores. The component does not alter the biological function of the bee. Of the aforementioned compounds, none is shared with this invention to inhibit the growth of *M. Plutonius, P. larvae* and *Nosema* spp.

"Treatment against bee *larvae* disease" ("Tratamiento contra la enfermedad de las larvas de las abejas") patent ES2215412T3: The document covers procedures and compositions for the cure and prevention of diseases in honeybees. The composition is an inoculation comprising one or more bacterial microorganisms and a delivery carrier. The procedure consists of inoculating the hive with the aforementioned composition. Consequently, in this patent it is proposed to use a mixture of microorganisms, of which none is shared with the present invention.

"Method for the control of infestations of honeybee colonies", patent WO197047193: This invention refers to a method to control several diseases in hives, by applying thereto, an effective amount of an essential oil in a slow release formulation, whereby the term oil includes, but is not limited to oils extractable from plants, or the essential component thereof, monoterpenes such as menthol, geraniol, thymol, myrcene citral, limonene, carene, camphor, eugenol or cineol (eucalyptol), natural oils such as lemon oil, eucalyptus oil or *Brickellia cavanillesii* oil, or organic acids such as formic acid, acetic acid or oxalic acid; the ones preferred most are monoterpenes like thymol or menthol, thymol however is preferred most of all. Consequently, in this patent it is proposed to use compounds, none of which is shared by this invention. Also their effectiveness against *P. larvae, M. Plutonius* and *Nosema* spp is not explained. The term pest refers to any organism that infects the bee colony.

"Novel composition apiary" patent WO2008132524: the composition comprises naturally occurring substances, the aqueous alcoholic extract of herbs (*Thymus vulgaris, Organum vulgare, Junglandis folium, Organum majoranna*) plus the addition of oils such as thymol, cinnamon and anise. Consequently, in this patent it is proposed to use compounds, none of which is shared by the present invention.

"Compositions and methods for prevention and treatment of diseases associated with honeybees" patent WO1997008954: The compositions of this invention are aqueous solutions comprising organic and inorganic acids and a chlorite ion. Optionally, the compositions may further comprise a gelling agent, a colorant and a preservative. Consequently in this patent, it is proposed to use compounds, none of which is shared by the present invention.

"Method, apparatus and compositions for the prophylaxis and treatment of colony collapse disorder" patent WO2013030854 A1: The invention relates to a method for preventing and treating Colony Collapse Disorder (CCD). It refers to a device which automatically delivers a replacement diet or as a natural food whose composition considers aqueous solutions comprising essential oils, none of which is shared by the present invention.

There is an article about a commercial *Olea europaea* leaf extract; however, its antimicrobial activity against any pathogen of *A. Mellifera* is not proven. "Antimicrobial activity of commercial *Olea europaea* (olive) leaf extract". Aurelia Sudjana N. et al., 2009. Other articles describe the antimicrobial activity of aqueous extracts and essential oils of plants against *P. larvae, M. Plutonius* and *Nosema ceranae*. None of them consider *Olea europaea*. Some of these articles are mentioned below.

"Laurel leaf extracts for honeybee pest and disease management: antimicrobial, microsporicidal, and acaricidal activity". N. Damiani et al., 2013.

"Antimicrobial activity of Scutia buxifolia against the honey bee pathogen *Paenibacillus larvae*" A. A Bolignon et al, 2013.

"Antimicrobial activity of Amazonian oils against *Paenibacillus* species". R. C. Santos et al, 2012.

In vivo evaluation of antiparasitic activity of plant extracts on *Nosema ceranae* (*Microsporidia*), M. Porrini et al, 2011.

"Antibacterial activity of water extracts and essential oils of various aromatic plants against *Paenibacillus larvae*, the causative agent of American Foulbrood". M. J. Gonzalez, J. M. Marioli, 2010.

"In vitro antibacterial effect of exotic plants essential oils on the honeybee pathogen *Paenibacillus larvae*, causal agent of American foulbrood" S. R. Fuselli et al, 2010.

Screening of natural compounds for the control of *nosema* disease in honeybees (*Apis mellifera*). L. Maistrello et al, 2008.

"Short communication. Inhibition of *Paenibacillus larvae* subsp *larvae* by the essential oils of two wild plants and their emulsifying agents" S. R. Fuselli., 2005.

The state of the art described herein reports compositions of herbal extracts and essential oils that do not include olive leaf extract with oleuropein as an active ingredient for the control of bee pathogens. Furthermore, from the patents mentioned only one of them proposes these extracts specifically for use in controlling American foulbrood and/or European foulbrood, so this invention is novel. In addition, the data reported is not sufficient for it to be obvious for an expert in the area, that the use of extract from olive leaves rich in oleuropein achieves controlling bacterial diseases and spores of *P. larvae*. As such, this invention is highly innovative. Finally, the authors of this invention have observed that the use of the composition comprising the extract of olive leaves rich in oleuropein controls the growth of *Melissococcus plutonius, Paenibacillus alvei* (secondary pathogen to the infection by *M. Plutonius*) and *Nosema* spp.

DRAWINGS

The figures described below are proposed with the aim of showing background information to support and serve as an example for the description of the composition; therefore they do not seek to restrict or in no way be considered as limiting the scope of the proposed development.

FIG. 1, the invention inhibits the growth of the vegetative cell of *P. larvae*

Vegetative cells were grown in the absence (A) and presence (B) of added extract diffusion disks. At 5 days, by visual inspection under a microscope, the bacterial growth around the paper disk was analyzed on culture plates (n=6).

Figure 2:
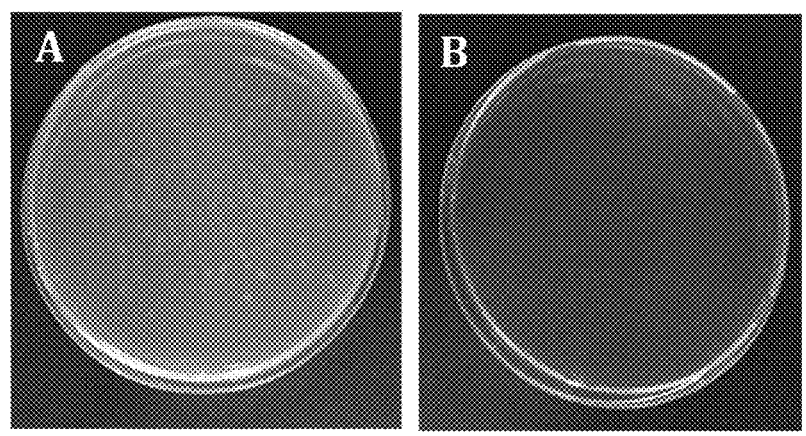

FIG. 2, the invention inhibits the growth of *P. larvae* spores.

The spores of *P. larvae* were exposed to the medium without extract (A), or to the medium supplemented with extract (B). At 5 days, the growth of colonies on culture plates (n=6) was analyzed by visual inspection.

Figure 3:
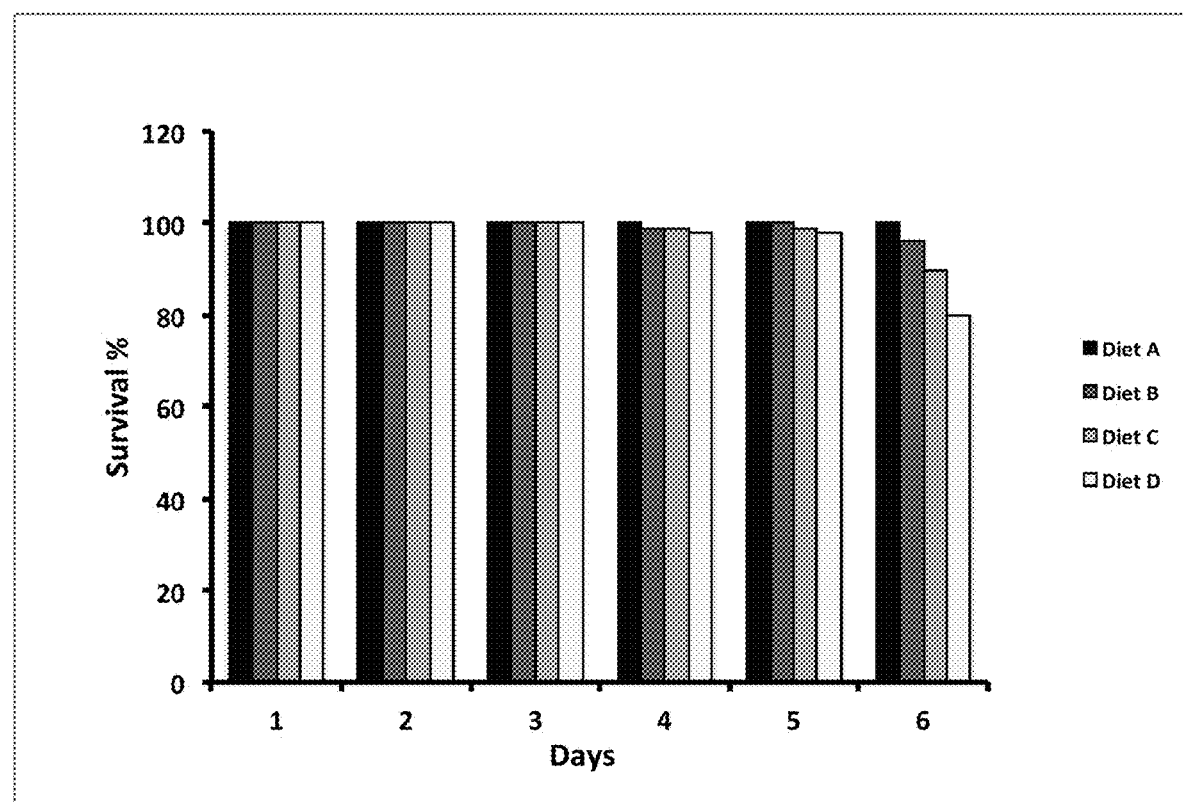

FIG. 3, the invention is not toxic for the *Apis mellifera larvae*, at different concentrations. *Larvae* were exposed to food without extract (diet A) and supplemented food with extract (diets B, C and D). After 5 days incubation, the larvae were analyzed by visual inspection and observation under optical microscope (n=2).

FIG. 4, the invention inhibits the growth of other pathogenic bacteria of *A. Mellifera. Melissococcus plutonius* and *Paenibacillus alvei* bacteria were exposed to the medium without extract and with extract. At 1, 2 and 5 days of incubation, the colony growth on culture plates was analyzed by visual inspection and under optical microscope (n=2).

FIG. 5, the invention does not inhibit the growth of other *Bacillus* and *Paenibacillus* present in the hives.

The bacteria *B. megaterium, B. subtilis, P. Polymyxa, B. pumilus*, were exposed to the medium without extract and with extract. At 1, 2 and 5 days, the colony growth on culture plates was analyzed by visual inspection and under optical microscope observation and colony growth on culture plates (n=2).

Figure 6:
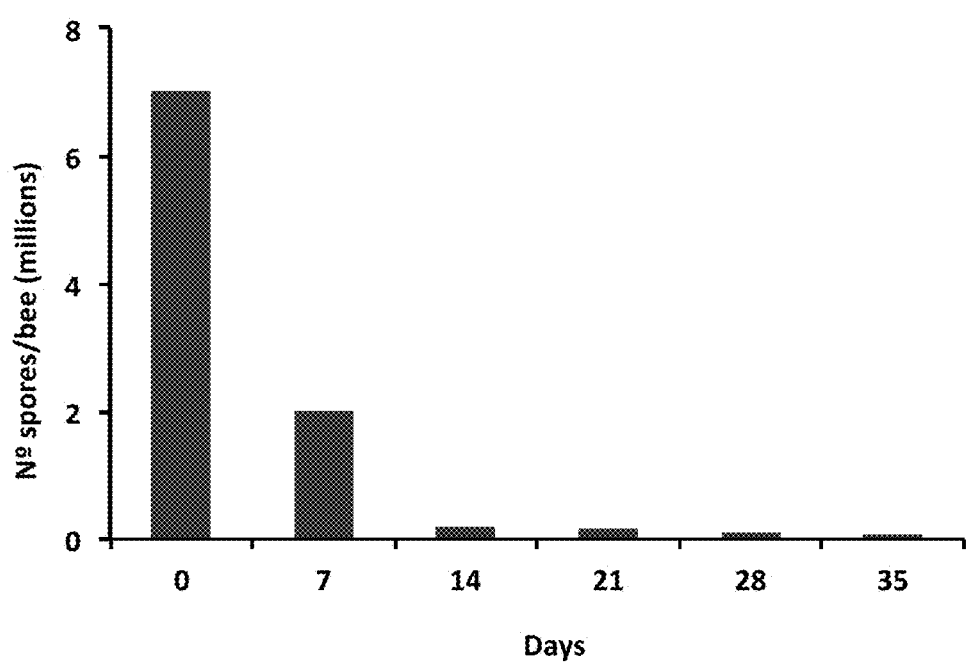

FIG. 6, the invention inhibits the proliferation and multiplication of *Nosema ceranae*.

Hives naturally infected with *N. Ceranae* were exposed to the extract. The rate of infection of spores purified from the stomachs of adult bees was analyzed by observation under an optical microscope at 7, 14, 21, 28 and 35 days post application. (n=1).

DETAILED DESCRIPTION OF THE INVENTION

The invention is related to a biocide composition for controlling pests affecting honeybees. The composition comprises a water soluble *Olea europaea* extract and a carrier. The preferred concentration of the extract in the biocide composition is in a range of concentration chosen from 0.001 to 40 mg/ml, 0.05 to 30 mg/ml, 0.05 to 0.08 mg/ml, 0.1 to 2 mg/ml, 2 to 10 mg/ml, 2 to 20 mg/ml and 2 to 40 mg/ml. Preferably, the range of concentrations of the extract in the biocide composition is 0.01 to 20 mg/ml. The concentration ranges which the biocide composition presents are important as they cover various uses for bee pest control. Some of these ranges can be used to control pests in their vegetative state, *Paenibacillus larvae* or *Melissococcus plutonius*; others however, can be used to control the states of spores, *P. larvae* or *Nosema* spp. Moreover, the biocide composition of this invention comprises an extract concentration range for use as a disinfectant. The concentrations of growth inhibition in the spore state are vital for the control of diseases; spores are the most aggressive infective stage of the American foulbrood or Nosemosis disease and thus directly affect the dynamics of the honeybee population in the beehive, causing losses in the honey production phase. As there is no effective treatment, outside the honey production season, both the hive's frames and box drawers, contaminated with spores, are stored until next season without being disinfected, becoming the source of infection at the start of the new production season, hence the relevant biocide treatment with a composition with a concentration range capable of removing bacteria along with fungal spores.

The concentration range in the composition can also be expressed not referring to the extract but to the main metabolite, Oleuropeia. In that case, the composition has a concentration range for Oleuropein of 0.0004 to 16 mg/ml, 0.02 to 12 mg/ml, from 0.02 to 0.032 mg/ml, 0.04 to 0.8 mg/ml, 0.8 to 4 mg/ml, 0.8 to 8 mg/ml and 0.8 to 16 mg/ml. Despite these calculations of the composition's concentration based on the major metabolite of the water soluble *Olea europaea* extract, it is important to stress the possible synergistic importance and biocide activity within the composition of the invention with the aqueous extract of the *Olea europaea's* leaves, which can have other metabolites present in lower proportions within the extract.

The biocide composition of the invention has the ability to control pests caused by *Paenibacillus larvae* (American foulbrood) either in their vegetative state or in the spore state. The composition is also capable of controlling *Melissococcus plutonius* (European foulbrood). In addition, it has been shown that the biocide composition of the invention is able to control the fungus, *Nosema* spp.

The biocide composition of the invention comprises a carrier with the necessary properties to give the composition the ability to be delivered in the hive, the hive's frames, the hive frame's screen and/or in the hive's feeder. This carrier of the composition can be a syrup, a wax, be liquid, powder or be a solid substrate. In a preferred embodiment of the invention the carrier is a syrup. This syrup consists of sucrose at a concentration in the ranges chosen from 10 to 600% w/v, 10-500% w/v, 20 to 400% w/v, 30 to 400% w/v, 30 to 200% w/v, 50-100% w/v.

The biocide composition also consists of one or more other biocides selected from one or more biocides from the group of: a synthetic organic biocide, a natural organic biocide and an inorganic biocide present in lower proportions within the extract.

From the additional biocides, these are chosen from one or more biocides from the group of: soybean essential oil, mugwort essential oil, eucalyptus oil, lemon oil, anise essential oil, cinnamon essential oil, black pepper essential oil, soapbark essential oil, rosemary essential oil, thyme essential oil, winter savory essential oil, celery essential oil, basil essential oil, bergamot essential oil, onion essential oil, cardamom essential oil, coriander essential oil, cypress essential oil, clove essential oil, cumin essential oil, turmeric essential oil, juniper essential oil, tarragon essential oil, geranium essential oil, fennel essential oil, frankincense essential oil, jasmine essential oil, laurel essential oil, mandarin essential oil, lemon balm essential oil, mint essential oil, oregano essential oil, rosemary essential oil, sage essential oil, sandalwood essential oil, thyme essential oil, turpentine essential oil, vanilla essential oil, valerian essential oil, *verbena* essential oil, carrot essential oil, garlic essential oil and combinations thereof.

The additional biocides in the composition used are selected from one or more biocides from the group of: soybean extract, mugwort extract, eucalyptus extract, lemon extract, anise extract, cinnamon extract, black pepper extract, soapbark extract, rosemary extract, thyme extract, winter savory extract, celery extract, basil extract, bergamot extract, onion extract, cardamom extract, coriander extract, cypress extract, clove extract, cumin extract, turmeric extract, juniper extract, tarragon extract, geranium extract, fennel extract, frankincense extract, jasmine extract, laurel extract, mandarin extract, lemon balm extract, mint extract, oregano extract, rosemary extract, sage extract, sandalwood extract, thyme extract, turpentine extract, vanilla extract, valerian extract, *verbena* extract, carrot extract, garlic extract and combinations thereof.

The additional biocide present in the composition may be chosen from one or more, which control pests of honeybees selected from the following ectoparasites and endoparasites: mites, such as *Varroa, Aethina tumida, Acarapis woodi, Tropilaelaps clareae, T. koenigerum*, fungi like *Ascosphaera apis, Aspergillus*, protozoa like *Malpighamoeba mellificae*, bacteria such as *Pseudomonas auriginosa*, viruses like the Sacbrood Bee Virus (SBV), Deformed Wing Virus (DWV), Kashmir Bee virus (KBV), Acute Bee Paralysis Virus (ABPV), Black Queen Cell Virus (BQCV), Chronic Bee Paralysis Virus (CBPV) or the Israeli Acute Paralysis Virus (IAPV).

One of the advantages of this invention is that the biocide composition has selectivity since it does not inhibit the growth, proliferation or survival of other bacteria characteristic of the hive. The proposed solution does not inhibit the growth, proliferation or survival of *Bacillus Megaterium, Bacillus Subtilis, Bacillus Pumilus* or *Paenibacillus Polymyxa*.

Another major advantage is that the composition of the invention contains concentrations of biocide that do not present adverse effects during any of the bee's stages of development.

The invention has no adverse effects during the larval development or on the adult bee. The proposed solution comprises the use of a water soluble *Olea europaea* leaf extract in a concentration range of 0.001 to 40 mg/ml, 0.05 to 30 mg/ml, 0.05 to 0.08 mg/ml, 0.1 to 2 mg/ml, 2 to 10 mg/ml, 2 to 20 mg/ml and 2 to 40 mg/ml and is a carrier. The concentration range used in the composition can also be expressed, not in reference to the extract but referring to the main metabolite Oleuropein. Preferably, the invention is related to the use of the biocide composition which comprises Oleuropein as the main metabolite in a range of concentration which runs from 0.0004 to 16 mg/ml, 0.02 to 12 mg/ml, from 0.02 to 0.032 mg/ml, 0.04 to 0.8 mg/ml, 0.8 to 4 mg/ml, 0.8 to 8 mg/ml and 0.8 to 16 mg/ml. Some of these ranges can be used to control pests in their vegetative state, *Paenibacillus larvae* or *Melissococcus plutonius*; others however, can be used to control the states of spores, *P. larvae* or *Nosema* spp. Moreover, the invention proposes the use of the biocide composition of the present invention as a disinfectant.

The invention is also related with the use of the biocide composition with the features described above comprising a carrier with the necessary properties that allow the composition to be used on the hive, on the hive's frames, on the hive frame's screens and/or on the hive's feeder. This carrier of the composition used can be a syrup, a wax, be liquid, powder or be a solid substrate. Preferably the carrier used in the composition is a syrup. This syrup consists of sucrose at a concentration in the ranges chosen from 10 to 600% w/v, 10-500% w/v, 20 to 400% w/v, 30 to 400% w/v, 30 to 200% w/v and 50-100% w/v.

The use of the invention may also comprise in the biocide composition consisting of the water soluble *Olea europaea* and a carrier, one or more other biocides selected from one or more biocides of the group of: a synthetic organic biocide, a natural organic biocide and an inorganic biocide present in lower proportions in the extract. Additional biocides in the composition used are chosen from one or more biocides of the group of: soybean essential oil, mugwort essential oil, eucalyptus oil, lemon oil, anise essential oil, cinnamon essential oil, black pepper essential oil, soapbark essential oil, rosemary essential oil, thyme essential oil, winter savory essential oil, celery essential oil, basil essential oil, bergamot essential oil, onion essential oil, cardamom essential oil, coriander essential oil, cypress essential oil, clove essential oil, cumin essential oil, turmeric essential oil, juniper essential oil, tarragon essential oil, geranium essential oil, fennel essential oil, frankincense essential oil, jasmine essential oil, laurel essential oil, mandarin essential oil, lemon balm essential oil, mint essential oil, oregano essential oil, rosemary essential oil, sage essential oil, sandalwood essential oil, thyme essential oil, turpentine essential oil, vanilla essential oil, valerian essential oil, *verbena* essential oil, carrot essential oil, garlic essential oil and combinations thereof.

Additional biocides in the composition used are chosen from one or more biocides from the group of: soybean extract, mugwort extract, eucalyptus extract, lemon extract, anise extract, cinnamon extract, black pepper extract, soapbark extract, rosemary extract, thyme extract, savory extract, celery extract, basil extract, bergamot extract, onion extract, cardamom extract, coriander extract, cypress extract, clove extract, cumin extract, turmeric extract, juniper extract, tarragon extract, geranium extract, fennel extract, frankincense extract, jasmine extract, laurel extract, mandarin extract, lemon balm extract, mint extract, oregano extract, rosemary extract, sage extract, sandalwood extract, thyme extract, turpentine extract, vanilla extract, valerian extract, *verbena* extract, carrot extract, garlic extract and combinations thereof.

The invention includes the use of an additional biocide which controls honeybee diseases, selected from the following ectoparasites and endoparasites: mites such as *Varroa, Aethina tumida, Acarapis woodi, Tropilaelaps clareae, T. koenigerum*, fungi like *Ascosphaera apis, Aspergillus*, protozoa like *Malpighamoeba mellificae*, bacteria like *Pseudomonas auriginosa*, virus such as the Sacbrood Bee Virus (SBV), Deformed Wing Virus (DWV), Kashmir Bee Virus (KBV), Acute Bee Paralysis Virus (ABPV), Black Queen Cell Virus (BQCV), Chronic Bee Paralysis Virus (CBPV) or the Israeli Acute Paralysis Virus (IAPV).

The proposed use in the invention has the advantage of presenting selectivity in its biocide effect, it does not inhibit the growth, proliferation or survival of the bacteria characteristic of the hive. The proposed solution does not inhibit the growth, proliferation or survival of *Bacillus Megaterium, Bacillus Subtilis, Bacillus Pumilus* or *Paenibacillus Polymyxa*. The invention can be used to spray, bathe and impregnate frame screens with the biocide composition on the hive, on the hive's frames, the frame's screen and/or the hive's feeder.

The invention consists in providing or preparing a biocide composition comprising an *Olea europaea* extract in water in a concentration range of 0.01 to 20 mg/ml and a carrier.

The application is also related to a method for controlling pests of bees comprising the steps of:

i) Preparing or providing a biocide composition comprising a water soluble *Olea europaea* extract in a concentration range of 0.01 to 20 mg/ml and a carrier.

ii) Incorporating *Olea europaea* extract to the hive's breeding chamber feeder, to the hive, to the hive frame's screen and/or to the hive's frame.

Preferably step ii) is done by spraying, dipping, impregnation or within the screening process of the frame.

The proposed solution comprises incorporating *Olea europaea* extract to the hive's breeding chamber feeder and/or in the screening of the hive's frame. The proposed solution is incorporated by spraying, dipping and impregnation.

The motive of this invention includes an apparatus which has impregnated the biocide composition. The apparatus of the invention is a hive, is a hive frame, is the screen of the hive's frame, is the hive's breeding chamber feeder.

The proposed invention also includes a kit comprising the biocide composition, as well as other components such as other biocides or user instructions. Preferably, in addition to the biocide composition, the kit comprises user instructions for the biocide composition of this invention for controlling honeybee infections.

The invention considers the biocide composition as part of a kit. The proposed solution also has as part of the kit, user instructions of the biocide composition.

EXAMPLES

The examples listed below are illustrative and are only incorporated to further the understanding of the specification and are not meant to limit in any way the scope of the claims requested.

Example 1

Growth Inhibition of *P. larvae* Vegetative Cells

The *P. larvae* vegetative cells were seeded at a density of $4\times10^6$ in a J solid culture medium, a paper disk (diffusion disk) was placed in the central area of each culture plate on *P. larvae* sown, with 10 µl of the carrier (without extract) or 10 µl of extract (50 mg/ml) and these were kept under microaerophilic conditions, $0_2/C0_2$ 5%/5-10% The direct observation of an inhibition halo around the diffusion disk considered growth inhibition. The inhibition zone was also observed under a microscope. At 5 days, the growth of *P. larvae* was evaluated. The inhibition halo on the plate which contained extract (FIG. 1) was observed. While on the plate that did not contain extract, the growth of *P. larvae* was not inhibited. Therefore, it was shown that the invention inhibits the growth of *P. larvae* vegetative cells.

Example 2

Growth Inhibition of *P. larvae* Spores

*P. larvae* spores were seeded at a density of 200 spores per culture plate in a solid J culture medium without extract and in a J medium with 6 mg/ml of extract and were kept under microaerophilic conditions $0_2/C0_2$ 5%/5-10% at 37 C. Growth inhibition was considered with the direct observation of the absence or reduction in the number of colonies of *P. larvae* on the plate with extract compared to the plate without extract. At 5 days, the growth of *P. larvae* was evaluated. Absence of colonies on the plate with extract was observed (FIG. 2). However, on the plate containing no extract, *P. larvae* colonies were observed. Thus, the invention is shown to be effective in inhibiting the growth of *P. larvae* spores.

Example 3

In Vitro Feeding of *Apis mellifera larvae* Using Different Concentrations of Extract

*Larvae* 12-24 hours after birth were fed with 10 µl of artificial diet, Diet A (12-18% glucose, 12-18% sucrose, 2-4% yeast extract, 50% royal jelly) or with 10 µl of artificial diet supplemented with extract at a final concentration range of 3 mg/ml (diet B), 5 mg/ml (diet C) and 10 mg/ml (diet D). Twenty four *larvae* in each condition were used to calculate the survival % from day 1 to 6 of incubation (FIG. 3). The dead *larvae* were identified according to three criteria: elasticity, size, color, food consumption and decomposition.

Example 4

Growth Inhibition of Other Bacteria, Characteristic to the Hive, in the Presence of Different Concentrations of Extract Bacteria *P. larvae, M. Plutonius, Paenibacillus alvei, Bacillus Megaterium, Bacillus Subtilis, Bacillus Pumilus* and *Paenibacillus polymyxa* were seeded at a density of $1\times10^6$ bacteria per culture plate and *P. larvae* spores at a density of 200 spores per culture plate in culture J or solid LB medium with extract and without extract in a range of concentration between 0.01 mg/ml and 25 mg/ml (inhibitor concentrations 1 to 12, FIG. 4) and between 0.01 mg/ml to 5 mg/ml (inhibitor concentrations 1 to 8, FIG. 5) in conditions similar to Example 2 or in anaerophyl 10% $C0_2$ at 35° C. Between day 1 and day 5 in incubation, it was evaluated whether the extract inhibited bacterial growth. All bacteria grew in the medium without extract. The absence of *P. larvae, M. plutonius* and *P. alvei* colonies was only observed in plates with extract; the invention is shown to be effective in a range of concentrations (FIGS. 4 and 5). These results allow concluding that the invention is applicable for other diseases that also attack the *larvae* of *A. Mellifera*, like European foulbrood whose causal agent is *M. Plutonius* and *P. alvei* as a secondary pathogen to the infection by *M. Plutonius.*

Example 5

The Administration of the Extract Resolves the Infection by *Nosema ceranae* in Adult Honeybees The extract (10 mg/ml) was administered to hives infected naturally with spores of *N. ceranae* at an infection rate of $7\times10^5$ spores/bee. The administration is performed once every 10 days. The infection rate was determined every 7 days. It was noted that at 7 days after the first administration, the rate of infection was reduced by 71% to ($2\times10^6$ spores/bee), reaching a reduction of 99% ($5\times10^3$ spores/bee) at 35 days post administration (FIG. 6).

BIBLIOGRAPHIC REFERENCES

Albo, G. N., E. Cerimele, M. S. Re, M. De Giusti, and A. M. Alippi. Logue americana: Ensayos de campo para evaluar la efectividad de algunos aceites esenciales. Vida Apicola (2001) 108:41-46.

Alippi, A. M., J. A. Ringuelet, E. L. Cerimele, M. S. Re, and C. P. Henning. Antimicrobial activity of some essential oils against *Paenibacillus larvae*, the causal agent of American Foulbrood disease. Journal of Herbs, Spices and Medicinal Plants (1996) 4:9-16.

Antunez, K., J. Harriet, L. Gende, M. Maggi, M. Eguaras, and P. Zunino. Efficacy of natural propolis extract in the control of American Foulbrood. Vet. Microbiol. (2008) 131:324-331.

Bastos, E. M., M. Simone, D. M. Jorge, A. E. Soares, and M. Spivak. In vitro study of the antimicrobial activity of Brazilian propolis against *Paenibacillus larvae*. J Invertebr. Pathol. (2008) 97:273-281.

Calderone, N. W., H. Shimanuki, and G. Allen-Wardell. An in vitro evaluation of botanical compounds for the control of the honeybee pathogen *Bacillus larvae* and *Ascosphera apis*, and the secondary invader *Bacillus alvei*. Journal essential oil research (1994) 6:279-286.

Damiani, N., Fernandez, N., Porrini, N., Gende, L, Alvarez, E., Buffa, F., Brasesco, C, Maggi, M., Marcangeli, J., Eguaras, M. Laurel leaf extracts for honeybee pest and disease management; antimicrobial, microsporicidal, and acaricidal activity. Parasitology Research (2013) DOI 10.1007/s00436-013-3698-3.

Eguaras, M. J., S. Fuselli, L. Gende, R. Fritz, S. R. Ruffinengo, G. Clement, A. Gonzalez, P. N. Bailac, and M. I. Ponzi. An in vitro evaluation of Tagetes minuta essential oil for the control of the honey bee pathogens *Paenibacillus larvae* and *Ascosphera apis*, and the parasitic mite *Varroa destructor*. Journal essential oil research (2005) 17:336-340.

Flesar, J., J. Havlik, P. Kloucek, V. Rada, D. Titera, M. Bednar, M. Stropnicky, and L. Kokoska. In vitro growth-inhibitory effect of plant-derived extracts and compounds against *Paenibacillus larvae* and their acute oral toxicity to adult honey bees. Vet. Microbiol. (2010) 145:129-133.

Forsgren, E., T. Olofssons, A. Vasquez, and I. Fries. Novel lactic acid bacteria inhibiting *Paenibacillus larvae* in honey bee *larvae*. Apidologie (2010) 41 :99-108.

Fuselli, S. R., S. B. Garcia de la Rosa, M. J. Eguaras, and R. Fritz. Chemical composition and antimicrobial activity of citrus essences on honeybee bacterial pathogen *Paenibacills larvae*, the causal agent of American foulbrood. World Journal Microbiology Biotechnology (2008) 24:2067-2072.

Fuselli, S. R., Garcia De La Rosa SB, L. B. Gende, M. J. Eguaras, and R. Fritz. Inhibition of *Paenibacillus larvae* employing a mixture of essential oils and thymol. Rev. Argent Microbiol. (2006) 38:89-92.

Gende, L. B., I. Floris, R. Fritz, and M. J. Eguaras. Antimicrobial activity of cinnamon (*Cinammomum zeylanicum*) essential oil and its main components again *Paenibacillus larvae* from Argentine. Bulletin Insectology (2008) 61:1-4.

Gonzalez, M. J. and J. M. Marioli. Antibacterial activity of water extracts and essential oils of various aromatic plants against *Paenibacillus larvae*, the causative agent of American Foulbrood. J Invertebr. Pathol. (2010) 104:209-213.

Maistrello, M., Lodesani, M., Costa, C, Leonardi, F., Marani, G., Caldon, M., Mutinelli, F., Granato, A. Screening of natural compounds for the control of *nosema* disease in honeybees (*Apis mellifera*). Apidologie (2008) 39:436-445.

Porrini, M. P., Fernandez, N., Garrido, P., Gende, L, Medici, S., Eguaras, M. In vivo evaluation of antiparasitic activity of plant extracts on *Nosema ceranae* (*Microsporidia*). Apidologie (201 1) 42:700-707.

Reynaldi, F. J., G. N. Albo, and A. M. Alippi. Effectiveness of tilmicosin against *Paenibacillus larvae*, the causal agent of American Foulbrood disease of honeybees. Vet. Microbiol. (2008) 132:1 19-128.

Roussenova, N. Antibacterial activity of essential oils against the etiological agent of american foulbrood disease (*Paenibacillus larvae*). Bulgarian Journal of Veterinary medicine (201 1) 14:17-24.

Santos, R. C, C. F. dos Santos Alves, T. Schneider, L. Q. Lopes, C. Aurich, J. L. Giongo, A. Brandelli, and A. de, V. Antimicrobial activity of Amazonian oils against *Paenibacillus* species. J Invertebr. Pathol. (2012) 109:265-268.

Vianna Santos, R. C, C. F. dos Santos Alves, T. Schneider, L. Q. Soares, C. Aurich, J. Luehring, A. Brandelli, and R. Vaucher. Antimicrobial activity of Amazonian oils against *Paenibacillus* species. Journal of Invertebrate Pathology (2012) 109:265-268.

Aliñe Bolignon, Thiele Faccim de Brum, Marina Zadra, mariana Piaña, Calilla Filippi dos Santos Alves, Viviane Pedroso, Valdir dos santos Barboza Júnior, Rodrigo de Almeida, Roberto Vianna santos, Margareth Linde. Antimicorbial activity of Scutia buxifolia against the honeybee pathogen *Paenibacillus larvae*. Journal of invertebrate Pathology (2013) 1 12:105-107.

The invention claimed is:

1. A method for controlling honeybees pests caused by *Paenibacillus larvae* spores and *Nosema ceranae* spores, comprising preparing or providing a biocide composition which comprises a water soluble *Olea europaea* leaf extract dissolved in a water solution in a concentration range of 2-10 mg/ml and a syrup, wherein the *Olea europaea* leaf extract has compounds obtained with ethanol and water as extraction solvents; and applying said biocide composition in a location.

2. The method of claim 1, wherein the location includes at least one of a hive, a frame of the hive, a screen of the frame of the hive, and/or a feeder of the hive.

3. The method of claim 1, wherein the syrup comprises sucrose at a concentration in the range of 20 to 400% w/v.

4. The method of claim 1, wherein the composition additionally comprises one or more biocides.

5. The method of claim 4, wherein the one or more biocides are selected from the group consisting of: a synthetic organic biocide, a natural organic biocide and an inorganic biocide.

6. The method of claim 4, wherein the one or more biocides are selected from the group consisting of: soybean extract, mugwort extract, *eucalyptus* extract, lemon extract, anise extract, cinnamon extract, black pepper extract, soapbark extract, rosemary extract, thyme extract, winter savory extract, celery extract, basil extract, bergamot extract, onion extract, cardamom extract, coriander extract, cypress extract, clove extract, cumin extract, turmeric extract, juniper extract, tarragon extract, geranium extract, fennel extract, frankincense extract, jasmine extract, laurel extract, mandarin extract, lemon balm extract, mint extract, oregano extract, rosemary extract, sage extract, sandalwood extract, thyme extract, turpentine extract, vanilla extract, *verbena* extract, carrot extract, garlic extract and combinations thereof.

7. The method of claim 1, wherein the application of the biocide composition in the location is done by at least one of: dipping or impregnating.

8. The method of claim 1, wherein the composition comprises the water soluble *Olea europaea* leaf extract dissolved in a water solution in a concentration of 6 mg/ml.

9. The method of claim 1, wherein the composition comprises the water soluble *Olea europaea* leaf extract dissolved in a water solution in a concentration of 10 mg/ml.

* * * * *